United States Patent [19]

Little et al.

[11] Patent Number: 5,283,822
[45] Date of Patent: Feb. 1, 1994

[54] BLACKLINE INDICATOR FOR USE IN TOMOGRAPHIC AND/OR RADIOSCOPIC INSPECTION OF WELD JOINTS

[75] Inventors: Francis H. Little, Cincinnati; Gerald B. Nightingale, West Chester, both of Ohio

[73] Assignee: General Electric Company, Cincinnati, Ohio

[21] Appl. No.: 953,151

[22] Filed: Sep. 29, 1992

[51] Int. Cl.⁵ .................................................. H05G 1/28
[52] U.S. Cl. ..................................... 378/162; 378/59; 378/207
[58] Field of Search ........................ 378/162, 207, 59

[56] References Cited

U.S. PATENT DOCUMENTS 3,521,059 7/1970 Stolle ................................. 378/162

Primary Examiner—Craig E. Church
Attorney, Agent, or Firm—Charles L. Moore, Jr.; Jerome C. Squillaro

[57] ABSTRACT

A blackline indictor for use in tomographic and/or radioscopic inspection of a weld joint is disclosed. The indicator includes a first elongated member having a first end and a second end and a second elongated member juxtaposed to said first member and also having a first end and a second end. The first ends of the elongated members are in contact with one another, and a spacer is disposed between the first and second members to position the second ends of the members at a selected distance from one another. The selected distance is at least equal to a thickness of the weld joint under inspection, and the first and second members and the spacer define a calibrated wedge shaped gap which is radiographically imageable to permit determination and control of the x-ray inspection parameters. The blackline indicator constituents may be magnetized to hold the constituents together and to permit attachment of the indicator to a workpiece under inspection in a position where the calibrated wedge shaped gap will be substantially superimposed over the weld joint in a radiographic image thereof with one of the elongated members being substantially parallel to the weld joint.

17 Claims, 2 Drawing Sheets

BLACKLINE INDICATOR FOR USE IN TOMOGRAPHIC AND/OR RADIOSCOPIC INSPECTION OF WELD JOINTS

BACKGROUND OF THE INVENTION

This invention relates to x-ray inspection, and more particularly, to a novel blackline indicator which can be radiographically imaged through a weld joint to facilitate determination and control of x-ray inspection system set-up parameters to provide appropriate spatial resolution and clarity for inspection of the weld joint to detect voids or other defects in the weld joint.

In tomographic and/or radioscopic inspection of a weld joint between two abutting pieces of material it is important to obtain parallelism between the x-ray beam central ray and the faces of the abutting pieces of a completed weld joint. This geometric alignment is critical because a misbond or lack of fusion at either or both side edges of the weld joint could escape detection if the x-ray beam were not precisely aligned with the joint and able to image the difference in thickness between a misbonded location and a properly fused location in the weld joint as seen along the x-ray beam path.

A presently used procedure for inspecting a weld joint between two components, such as two cylindrically shaped shafts which are butted end to end and welded together at their abutting faces, involves tack welding the two abutting faces at a plurality of locations around the circumference of the two shafts. A reference datum, such as a shoulder block or collar, which can be radiographically or radioscopically imaged with the joint, is required on one of the shafts at a predetermined distance from the tack welded joint. If a shoulder or similar feature is not already present, which may be used as a datum, such a surface feature must be attached to one of the shafts. The tack welded joint is then x-rayed to provide a radiographic image to verify the alignment of the x-ray beam relative to the plane of the tack welded joint. When the gap or "blackline" between the two abutting faces of the shafts are properly imaged with appropriate clarity and spatial resolution, the precise x-ray geometric set-up and parameters used to provide this image will be used for the actual weld joint inspection after the weld joint has been completely welded. The reference block or collar is used to properly position and align the finished weld joint within the x-ray fan beam for final inspection. After final x-ray inspection, the reference block or collar must be removed. This procedure, therefore, requires additional steps in order to properly inspect the weld joint. For example, the reference block or collar must be attached; the joint must be tack welded and radiographically imaged to provide a pre-inspection or "blackline" image to verify proper set-up of the x-ray system to provide appropriate x-ray inspection images with adequate spatial resolution after the final welding operation; and the reference collar or block must be removed. These additional steps reduce the cycle time and increase the expense of inspecting the component.

Additionally, if radioscopic images of the interior of the welded joint are desired, a "blackline" image may not be useful or appropriate for determining the appropriate x-ray system parameters or computed tomography (CT) parameters because of the close proximity of the x-ray source relative to the weld joint and because of the dynamic nature of the inspection process in which the x-ray source and detector or the weld joint are moved relative to one another to permit gathering of the data to provide the CT image.

SUMMARY OF THE INVENTION

It is accordingly a primary object of the present invention to provide a novel blackline indicator for use in tomographic and/or radioscopic inspection of weld joints.

It is another object of the present invention to provide a novel blackline indicator which eliminates the additional steps needed to generate a pre-inspection blackline image of a weld joint to facilitate determination of the x-ray system parameters.

In accordance with the present invention, a blackline indicator for use in radiography and radioscopy of a weld joint includes a first elongated member having a first end and a second end and a second elongated member juxtaposed to said first member and also having a first end and a second end. The first ends of each elongated member are in contact with each other. A spacer, such as a gauge pin or the like, is disposed between the first and second elongated members to position the second ends of the elongated members at a selected distance from one another. The selected distance is preferably at least equal to a thickness of the weld joint under inspection, and the first and second members and the spacer define a calibrated wedge shaped gap which is radiographically imageable to permit determination and control of the x-ray inspection parameters. The blackline indicator constituents may be magnetized to hold the constituents together and to permit attachment of the indicator to a workpiece under inspection in a position where the wedge shaped gap can be imaged through the weld joint to permit adjustment of the x-ray system parameters and can be easily removed before final inspection using the system parameters determined from the blackline indicator image.

Other objects of the invention, together with features and advantages thereof, will become apparent from the following detailed specification when read with the accompanying drawings in which like referenced numerals refer to like elements.

DETAILED DESCRIPTION OF THE PREFERRED EMBODIMENTS

Figure 1:
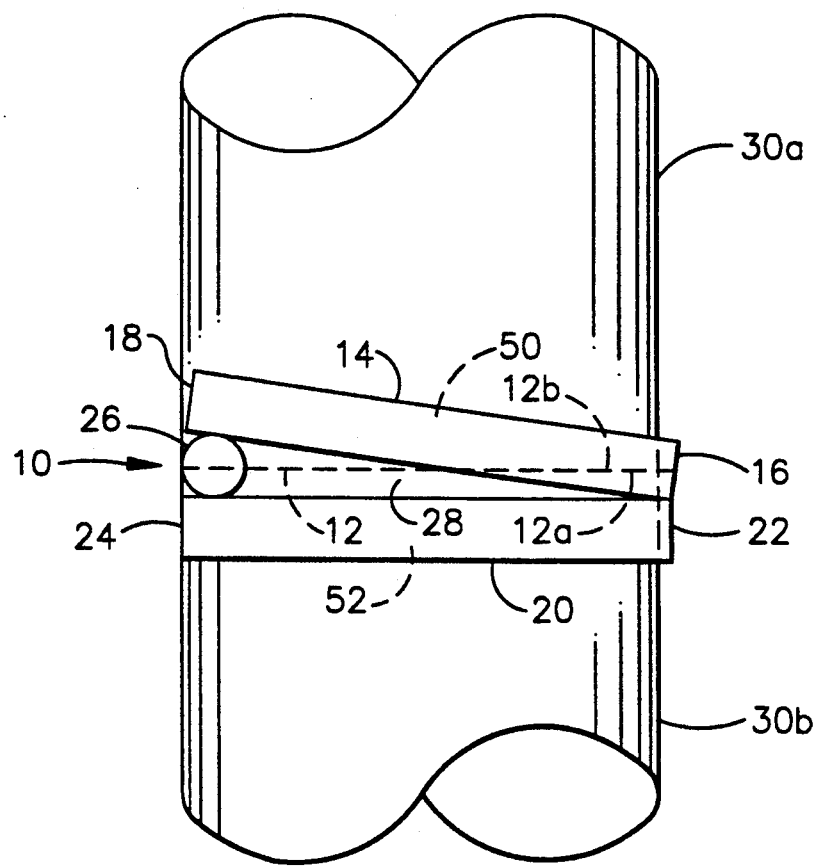
FIG. 1 is a side elevation view of the blackline indicator in accordance with one embodiment of the present invention.

Referring initially to FIG. 1, a blackline indicator 10 for use in tomographic and/or radioscopic inspection of a weld joint 12 includes a first flat, elongated member 14 having a first end 16 and a second end 18 at opposite longitudinal ends thereof. A second flat elongated member 20 is juxtaposed to said first member 14 and also has a first end 22 and a second end 24 at opposite longitudinal ends thereof. The first ends 16 and 22 of each of the elongated members 14 and 20 are in contact with each other. A spacer 26, such as a gauge pin or gauge bar, is disposed between the first and second members 14 and 20 proximate to the second ends 18 and 24 thereof. The spacer 26 has a predetermined diameter or size to position the second ends 18 and 24 at a selected distance from one another. The selected distance is preferably at least equal to the thickness of the weld joint 12 under inspection, and the inner edges 14a and 20a of the first and second members 14 and 20 along with spacer 26 define a calibrated wedge shaped gap 28 which is radiographically imageable to permit determination and control of x-ray inspection parameters, such as x-ray power, spatial resolution, orientation of the x-ray fan beam and detector relative to a plane defined by the abutting faces 12a and 12b of workpiece components 30a and 30b, and the like.

The first and second elongated members 14 and 20 should be made from a material having a density as great as or greater than that of the workpiece 30 under inspection to provide good contrast in the image so that the first and second elongated members 14 and 20 will be radiographically imageable and the calibrated wedge shaped gap will be clearly bounded by the members 14 and 20 for determination and control of the x-ray inspection parameters.

In one embodiment of the present invention, the first and second members 14 and 20 are also preferably magnetized to hold the members and spacer 26 in place during generation of a blackline image and to also permit attachment of the indicator 10 to a ferromagnetic workpiece 30 under inspection in a position where the calibrated wedge shaped gap 28 will be substantially superimposed over the weld joint 12 with one of the inner edges 14a or 20a of the elongated members 14 or 20 parallel to the weld joint 12 in a radiographic image of the workpiece 30. As an alternative to magnetizing the indicator 10, or if the workpiece 30 under inspection is made from a non-ferromagnetic material, a strap arrangement 32 as illustrated by the broken line 32 in FIG. 3 may be used to hold the blackline indicator 10 in relation to the workpiece 28 under inspection during generation of a blackline image. The strap 32 should be made from a material having a density significantly less than that of the indicator 10 and the workpiece 30 so that the strap 32 will not appear in the radiographic image and interfere with the inspection.

The spacer 26 should have a diameter or size at least equal to if not larger than the thickness of the weld joint 12. Typically, spacer 26 may be a gauge pin having a diameter between about 1 and about 10 mils. Those skilled in the art will, therefore, recognize that the indicator 10 is capable of providing a radiographic image which represents a range of voids or defects which might be present in the weld joint 12 from the maximum expected void or defect at the location of elongated member second ends 18 and 24 to where the gap 28 tapers to a representation of no voids or gaps at the location where first ends 16 and 22 contact one another. The indicator 10 functions to demonstrate spatial resolution in the radiographic image by its ability to provide clear images of the inner edges 14a and 20a along their diminishing spatial difference from the second ends 18 and 4 to the first ends 16 and 22. The indicator 10 thus provides an indication of the defect size detectability and may permit relaxation of manufacturing requirements because of the higher confidence of defect detectability in weld joints.

Figure 3:
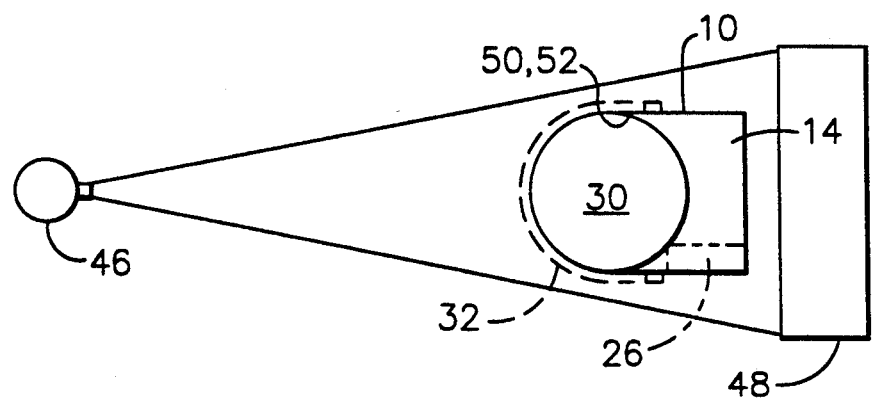
FIG. 3 is a top view of the blackline indicator of the present invention shown in relation to the component under inspection and the x-ray source and detector of an x-ray system.

In operation, the blackline indicator 10 may be radiographically imaged through the weld joint 12 in workpiece 30 as best shown in FIG. 3 to properly set the x-ray parameters, including geometric alignment, to provide an appropriate image of the gap 28 along its entire length from the maximum defect representation to the no defect representation where ends 16 and 22 contact one another. The blackline indicator 10 is then removed and a final radiographic inspection image of the weld joint 12 is generated with the same x-ray parameters which were determined using the blackline indicator 10. Thus, a high confidence level exists that the entire range of potential defects from the maximum size void to the no defect situation would be clearly imaged by the x-ray system.

Figure 2:
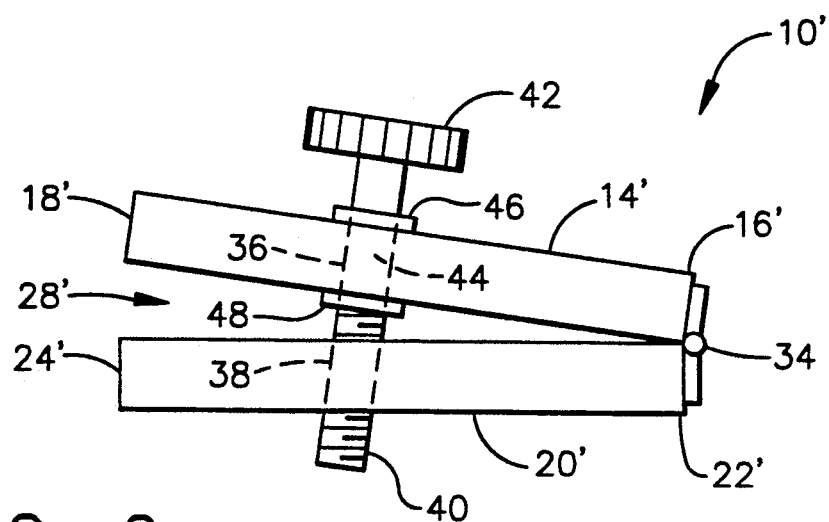
FIG. 2 is a side elevation view of a blackline indicator in accordance with another embodiment of the invention.

Referring to FIG. 2, another embodiment of the blackline indicator 10' of the present invention includes a first flat elongated member 14' with a first end 16' and a second end 18' at opposite ends of the elongated member 14'. A second flat elongated member 20' is juxtaposed to the first flat elongated member 14' and has a first end 22' and a second end 24' at opposite ends of the elongated member 20'. The respective first ends 16' and 22' contact one another and elongated members 14' and 20' are pivotably mounted to each other by their respective first ends 16' and 22' by a suitable hinge arrangement 34 or the like. The first elongated member 14' has a bore 36 formed therethrough and second elongated member 20' also has a bore 38 formed therethrough which is threaded to receive a threaded portion 40 of a thumbscrew 42. Another portion 44 of thumbscrew 42 is captured in bore 36 and is rotatable therein to permit adjustment of the selected distance between second ends 18' and 24' when the thumbscrew is turned in one direction to draw the second ends 18' and 24' toward one another and in an opposite direction to force the second ends 18' and 24' away from one another. Thumbscrew 42 may be captured in bore 36 by collars 46 and 48. Bore 36 may be slightly oversized relative to thumbscrew portion 44 to permit some movement of the thumbscrew portion 44 within the bore 36 during adjustment of the selected distance between second ends 18' and 24' and the calibrated wedge shaped gap 28'. Thumbscrew 42 should be made from a material which has a density which is substantially less than that of the indicator 10' and the workpiece 30 under inspection.

FIG. 3 shows an example of the blackline indicator 10 of the present invention in its operating environment. The blackline indicator 10 is typically positioned behind the workpiece 30 under inspection relative to the x-ray source 46 and between the workpiece 30 and the x-ray detector 48 to permit imaging of the blackline indicator 10 through the workpiece 30. The first and second members 14 and 20 have respective side edges 50 and 52 which may be shaped to matingly abut a surface of the workpiece 30. For example, the side edges 50 and 52 may be substantially arcuately shaped with a predetermined radius to matingly abut a cylindrical shaft 30, as shown in FIG. 3, to superimpose the calibrated wedge shaped gap 28 over the weld joint 12 (FIG. 1) joining the two portions 30a and 30b of the shaft 30. As previously discussed, the x-ray parameters, such as power, focal point, distances between x-ray source 46 and detector 48 relative to workpiece 30 and geometric alignment are determined, to provide appropriate spatial resolution. After these parameters have been determined, the blackline indicator 10 is removed and a final x-ray inspection image of the workpiece 30 is generated. Because the x-ray system has been set up to properly image the full range of expected defect sizes using the blackline indicator 10, any such defects should be appropriately represented on the final inspection image of the workpiece 30.

It will be readily understood by those skilled in the art that the present invention is not limited to the specific embodiments described and illustrated herein. Different embodiments and adaptations besides those shown herein and described, as well as many variations, modifications and equivalent arrangements will now be apparent or be reasonably suggested by the foregoing specification and drawings without departing from the substance or scope of the invention. While the present invention is described herein in detail in relation to its preferred embodiments, it is to be understood that this disclosure is only illustrative and exemplary of the present invention and is made merely for purposes of providing a full and enabling disclosure of the invention. Accordingly, it is intended that the invention is limited only by the spirit and scope of the claims appended hereto.

What is claimed is:

1. A blackline indicator for use in tomographic and radioscopic inspection of a weld joint, comprising:
   a first elongated member having a first and a second end;
   a second elongated member juxtaposed to said first member and having a first end and a second end, said first end being in contact with said first end of said first member; and
   spacer means disposed between said first and second members to position said second ends thereof at a selected distance from one another, said selected distance being at least equal to a thickness of the weld joint under inspection, and said first and second members and said spacer means defining a calibrated wedge shaped gap which is radiographically imageable to permit determination and control of x-ray inspection parameters.

2. The blackline indicator of claim 1, wherein said first and second elongated members are made from a material having a density at least as great as a workpiece containing the weld joint under inspection.

3. The blackline indicator of claim 1, further comprising means for attaching said indicator to a workpiece under inspection in a position where said calibrated wedge shaped gap will be substantially superimposed over the weld joint in a radiographic image thereof.

4. The blackline indicator of claim 1, wherein said indicator is magnetized to hold said first and second members together and to permit attachment of said indicator to a workpiece under inspection in a position where said calibrated wedge shaped gap will be substantially superimposed over the weld joint in a radiographic image thereof.

5. The blackline indicator of claim 1, further comprising means for fastening said first and second members together to define said calibrated wedge shaped gap.

6. The blackline indicator of claim 5, wherein said fastening means includes a threaded thumbscrew received in a matingly threaded bore formed in one of said first and second members and said threaded thumbscrew extending through a bore formed in the other of said first and second members and rotatably captured therein to permit adjustment of said second ends to a different selected distance when said thumbscrew is turned in one direction to draw said second ends toward one another and in an opposite direction to force said second ends away from one another.

7. The blackline indicator of claim 6, wherein said first ends are pivotably mounted to each other.

8. The blackline indicator of claim 1, wherein said spacer means is a gauge pin having a diameter of between about 1 and about 10 mils.

9. The blackline indicator of claim 1, wherein said first and second members have respective side edges which bound said calibrated wedge shaped gap, said side edges being shaped to matingly abut a workpiece surface to substantially superimpose said calibrated wedge shaped gap over the weld joint.

10. The blackline indicator of claim 1, wherein said side edges are substantially arcuately shaped at a selected radius to matingly abut a cylindrical shaft and substantially superimpose said calibrated wedge shaped gap over a weld joint joining two portions of said shaft.

11. A blackline indicator for use in tomographic and radioscopic inspection of a weld joint, comprising:
    a first elongated member having a first and a second end;
    a second elongated member juxtaposed to said first member and having a first end and a second end, said first end being in contact with said first end of said first member; and
    means for positioning said second ends at a predetermined distance from one another to define a calibrated wedge shaped gap which is radiographically imageable to permit determination and control of x-ray inspection parameters.

12. The blackline indicator of claim 11, wherein said first and second elongated members are made from a material having a density at least as great as a workpiece containing the weld joint under inspection.

13. The blackline indicator of claim 11, further comprising means for attaching said indicator to a workpiece under inspection in a position where one of said elongated members will be substantially parallel to the weld joint under inspection.

14. The blackline indicator of claim 11, wherein said positioning means is adjustable to permit positioning of said second ends at a multiplicity of different predetermined distances from one another to define a multiplicity of respective different size wedge shaped gaps.

15. The blackline indicator of claim 11, wherein said first ends are pivotably mounted to each other.

16. The blackline indicator of claim 11, wherein said predetermined distance corresponds substantially to a thickness of the weld joint under inspection.

17. The blackline indicator of claim 11, wherein said first and second members have respective side edges which bound said calibrated wedge shaped gap, said side edges being shaped to matingly abut a workpiece surface in a position where one of said elongated members will be substantially parallel to the weld joint under inspection.

* * * * *